United States Patent [19]
Eastin

[11] Patent Number: 5,974,734
[45] Date of Patent: Nov. 2, 1999

[54] SOLID MATRIX PRIMING OF SEEDS WITH MICROORGANISMS AND SELECTED CHEMICAL TREATMENT

[75] Inventor: John Alvin Eastin, Lincoln, Nebr.

[73] Assignee: Kamterer II, LLC, Lincoln, Nebr.

[21] Appl. No.: 08/854,500

[22] Filed: May 12, 1997

Related U.S. Application Data

[63] Continuation-in-part of application No. 08/369,308, Jan. 6, 1995, Pat. No. 5,628,144, which is a continuation-in-part of application No. 07/975,410, Nov. 10, 1992, abandoned, which is a continuation-in-part of application No. 07/503,826, Apr. 3, 1990, abandoned, which is a continuation-in-part of application No. 07/440,470, Nov. 20, 1989, abandoned, which is a continuation of application No. 07/175,934, Mar. 30, 1988, abandoned, which is a continuation-in-part of application No. 07/034,812, Apr. 3, 1987, Pat. No. 4,912,874.

[51] Int. Cl.$^6$ .......................... A01B 79/00; A01C 21/00; C05F 3/00; A01N 63/00
[52] U.S. Cl. .......................... 47/58.1; 47/57.6; 47/DIG. 9; 47/DIG. 10; 71/13; 424/93.1
[58] Field of Search .................................. 47/58.1, 57.6, 47/DIG. 9, DIG. 10; 71/13; 424/93.1

[56] References Cited

U.S. PATENT DOCUMENTS

| | | |
|---|---|---|
| 835,708 | 11/1906 | Mikorey . |
| 1,795,875 | 3/1931 | Maynard . |
| 1,828,463 | 10/1931 | Hammers . |
| 1,981,077 | 11/1934 | Shields . |
| 2,364,264 | 12/1944 | Yeomans . |
| 2,460,884 | 2/1949 | Hjort et al. . |
| 2,566,392 | 9/1951 | Wilkins et al. . |
| 2,754,151 | 7/1956 | Williamson . |
| 2,901,182 | 8/1959 | Cragg et al. . |
| 2,966,056 | 12/1960 | Heller . |
| 2,966,057 | 12/1960 | Heller . |
| 3,015,842 | 1/1962 | Stalego . |
| 3,095,152 | 6/1963 | Westdahl . |
| 3,133,445 | 5/1964 | Richard . |
| 3,201,047 | 8/1965 | Danberg . |
| 3,249,307 | 5/1966 | Peeps et al. . |
| 3,258,207 | 6/1966 | Cody . |
| 3,372,319 | 3/1968 | Rhodes . |
| 3,458,138 | 7/1969 | Yankee . |
| 3,469,157 | 9/1969 | Rhodes . |
| 3,473,096 | 10/1969 | Johnson et al. . |
| 3,521,402 | 7/1970 | Chaffee et al. ........................ 47/58 |
| 3,538,403 | 11/1970 | Carollo . |
| 3,565,345 | 2/1971 | Moltzan . |
| 3,584,412 | 6/1971 | Palmer . |
| 3,592,386 | 7/1971 | Tschody, Jr. . |
| 3,633,550 | 1/1972 | Kraus . |
| 3,680,039 | 7/1972 | Tsao . |
| 3,723,989 | 3/1973 | Fathauer . |
| 3,747,058 | 7/1973 | Okamoto et al. . |
| 3,748,576 | 7/1973 | Sigournay . |
| 3,750,955 | 8/1973 | Nakai et al. . |
| 3,779,070 | 12/1973 | Cushman et al. . |
| 3,822,825 | 7/1974 | Dupre . |
| 3,844,485 | 10/1974 | Waggoner . |
| 3,846,559 | 11/1974 | Poteet, III . |
| 3,881,353 | 5/1975 | Fathauer . |
| 3,881,631 | 5/1975 | Loesch et al. . |
| 3,912,121 | 10/1975 | Steffen . |
| 3,920,153 | 11/1975 | Saito . |
| 3,921,159 | 11/1975 | Steffen . |
| 3,927,400 | 12/1975 | Knepler . |
| 3,928,751 | 12/1975 | Fathauer . |
| 3,974,377 | 8/1976 | Steffen . |
| 4,009,799 | 3/1977 | Fathauer . |
| 4,022,058 | 5/1977 | Brown et al. . |
| 4,054,779 | 10/1977 | Wilke . |
| 4,056,970 | 11/1977 | Sollish . |
| 4,057,709 | 11/1977 | Lyngsgaard et al. . |
| 4,079,362 | 3/1978 | Grimm et al. . |
| 4,100,538 | 7/1978 | Knepler . |
| 4,137,529 | 1/1979 | Anson et al. . |
| 4,149,163 | 4/1979 | Fathauer . |
| 4,159,064 | 6/1979 | Hood . |
| 4,163,507 | 8/1979 | Bell . |
| 4,164,669 | 8/1979 | Knepler . |
| 4,165,458 | 8/1979 | Koizumi et al. . |
| 4,166,948 | 9/1979 | Steffen . |
| 4,181,241 | 1/1980 | Currah . |
| 4,211,506 | 7/1980 | List et al. . |
| 4,224,882 | 9/1980 | Cruse . |
| 4,225,930 | 9/1980 | Steffen . |
| 4,238,790 | 12/1980 | Balogh et al. . |
| 4,239,010 | 12/1980 | Amburn . |

| | | |
|---|---|---|
| 4,246,469 | 1/1981 | Maria . |
| 4,268,825 | 5/1981 | Kaplan . |
| 4,277,833 | 7/1981 | Steffen . |
| 4,307,390 | 12/1981 | Steffen et al. . |
| 4,316,625 | 2/1982 | Goon et al. . |
| 4,329,571 | 5/1982 | Gerig et al. . |
| 4,333,096 | 6/1982 | Jenkins et al. . |
| 4,369,895 | 1/1983 | McCarty et al. . |
| 4,379,106 | 4/1983 | Bussey, Jr. et al. . |
| 4,407,450 | 10/1983 | Chegolya et al. . |
| 4,410,106 | 10/1983 | Kierbow et al. . |
| 4,410,139 | 10/1983 | Nishikawa et al. . |
| 4,441,101 | 4/1984 | Robar . |
| 4,455,111 | 6/1984 | Jackson et al. . |
| 4,455,288 | 6/1984 | Salter et al. . |
| 4,459,144 | 7/1984 | Van Pelt et al. . |
| 4,463,345 | 7/1984 | Okkerse et al. . |
| 4,468,795 | 8/1984 | Gerig . |
| 4,491,241 | 1/1985 | Knepler et al. . |
| 4,516,229 | 5/1985 | Kearns . |
| 4,587,772 | 5/1986 | Griffiths . |
| 4,632,284 | 12/1986 | Erazo et al. . |
| 4,798,723 | 1/1989 | Dart et al. .................................. 424/93 |
| 4,912,874 | 4/1990 | Taylor . |
| 5,628,144 | 5/1997 | Eastin .......................................... 47/58 |

FOREIGN PATENT DOCUMENTS 848060  10/1984  South Africa .

OTHER PUBLICATIONS

U.S. Dept. of Agriculture, Agriculture Information Bulletin 409; "Growing Your Own Vegetables", Dec., 1977.
Anwar A. Khan, et al., "Osmoconditioning of Beet Seeds to Improve Emergence and Yield in Cold Soil", *Agronomy Journal,* vol. 75, No. 5, Sep.–Oct. 1983; pp. 788–794.
A. A. Khan, et al., "Matriconditioning of Seeds to Improve Emergence" Abstract, Stand Establishment of Horticultural Crops Symposium, Apr. 4–6, 1990, pp. 19–40.
Kent J. Bradford, "Seed Priming: Techniques to Speed Seed Germination", Proceedings of the Oregon Horticultural Society 1984, vol. 25, pp. 227–233.
Walter H. Gardner, Washington State University, Pullman, WA; "Water Content", Chapters 7–9, pp. 82–163.
Thomas Greweling & Michael Peech, "Chemical Soil Tests", *Cornell University Agricultural Experiment Station,* New York State College of Agriculture, Ithaca, NY, Bulletin 960, Nov. 1960.
P. Coolbear, et al., "Osmotic pre–sowing treatments and nucleic acid accumulation in tomato seeds (*Lycopersicon lycopersicum*)", *Seed Sci. & Technol.,* 1980, 8, pp. 289–303.
Anna Szafirowska, et al., "Osmoconditioning of Carrot Seeds to Improve Seedling Establishment and Yield in Cold Soil", *Agronomy Journal,* vol. 73, Sep.–Oct., 1981, pp. 845–848.
A. M. Haigh, et al., "Field Emergence of Tomato, Carrot, and Onion Seeds Primed in an Aerated Salt Solution", *J. Amer. Soc. Hort. Sci.* 111 (5):660–665, 1986.
Daniel J. Cantliffe, et al., "Mechanism of Seed Priming in Circumventing Thermodormancy in Lettuce", *Plant Physiol.* (1984) 75, 290–294.
T. W. Hegarty, "Seed Activation and Seed Germination Under Moisture Stress", *New Phytol.* (1977) 78, 349–359.
Kauser A. Malik & F. Azam, "Effect of Humic Acid on Wheat (*Triticum Aestivum* L.) Seedling Growth", *Environmental and Experimental Botany,* vol. 25, No. 3, pp. 245–252, 1985.
Suhas R. Ghate, et al., "Seeding Pre–Germinated Vegetable Seeds in Plots", *Transactions of the ASAE,* 1981, pp. 1099–1102.
S. M. Ward, "Performance of a Prototype Fluid Drill", *J. agric. Engng Res.,* 1981, 26, pp. 321–331.
D. Gray, "Fluid Drilling of Vegetable Seeds", *Horticultural Review,* vol. 3, 1981, Chapter 1, pp. 1–27.
G. Stotzky, "Influences of Soil Mineral Colloids on Metabolic Processes, Growth, Adhesion, and Ecology of Microbes and Viruses", *Microbial Events in Soil,* Chapter 10, pp. 305–428.
National Veg. Res. St., "Fluid Drilling", *Annual Reports,* 1972–84.
Dr. W. E. Finch–Savage, "Vegetable Crops: Some Advantages of Fluid Drilling", *Span,* 26.1.1983; pp. 7–9.
James E. Ells, "The Influence of Treating Tomato Seed with Nutrient Solutions on Emergence Rate and Seedling Growth", *Ells: Tomato Seed Treatment and Germination,* pp. 684–687.
Heydecker, et al., "Invigoration of seeds?", *Seed Sci. & Technol.,* 3, 1975, pp. 881–888.
I. Chet, et al., "Mechanisms of biocontrol of soil–borne plant pathogens by Rhizobacteria", *The rhizosphere and plant growth,* 1991, pp. 229–236.
John Davison, "Plant Beneficial Bacteria", *Bio/Technology,* vol. 6, Mar. 1988, pp. 282–286.
Heydecker et al. Seed Sci. Technol. 5:353–425, 1977.

*Primary Examiner*—Ponnathapu Achutamurthy
*Assistant Examiner*—Tekchand Saidha
*Attorney, Agent, or Firm*—Vincent L. Carney

[57]     ABSTRACT

In the process of the invention, the seed to be treated, a predetermined amount of solid matrix material and a predetermined amount of water are admixed and the mixture allowed to stand, preferably in a container which allows entry of air but which reduces evaporation losses, for example, a closed metal container with a small top opening, for a time and at a temperature sufficient to enhance resultant plant vigor, i.e., enhance emergence, growth of yield characteristics, but short of that which would cause the seed to sprout. Faulty seeds may be separated by size and systemic resistance to disease can be induced.

7 Claims, 5 Drawing Sheets

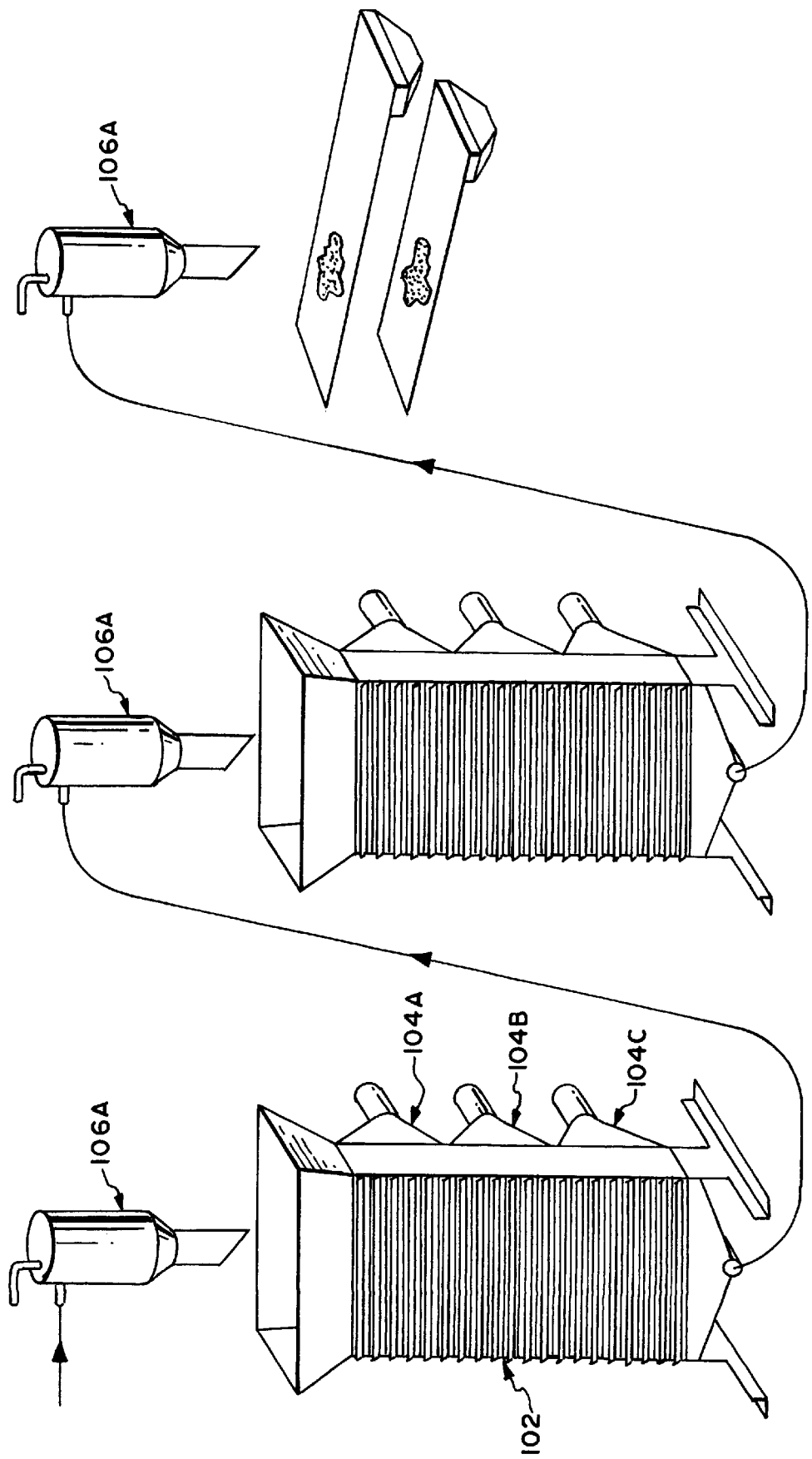

SOLID MATRIX PRIMING OF SEEDS WITH MICROORGANISMS AND SELECTED CHEMICAL TREATMENT

RELATED CASES

This application is a continuation-in-part of U.S. application Ser. No. 08/369,308 now U.S. Pat. No. 5,328,144 filed Jan. 1, 1995, which is a continuation-in-part of U.S. application Ser. No. 07/975,410 filed Nov. 10, 1992, now abandoned, which is a continuation-in-part of U.S. application Ser. No. 07/503,826 filed Apr. 3, 1990, now abandoned, which is a continuation-in-part of U.S. application Ser. No. 07/440,470 filed on Nov. 20, 1989, now abandoned, which is a continuation of U.S. application Ser. No. 07/175,934 filed Mar. 30, 1988 now abandoned, which is a continuation-in-part of U.S. patent application Ser. No. 07/034,812 filed Apr. 3, 1987, entitled SOLID MATRIX PRIMING OF SEEDS, now U.S. Pat. No. 4,912,874.

BACKGROUND OF THE INVENTION

This invention relates to the conditioning of seeds, such as for example, by priming, chemical treatment and biological treatment and to the use of biologically treated seeds to recondition land and improve plant productivity.

Seed priming or osmoconditioning are terms to describe a known pre-sowing hydration treatment developed to improve seedling establishment (Heydecker and Coolbear, 1977, *Seed Science and Technology* 5:353– 425), (Khan, et al., 1980/81, *Israel J. Bot.* 29:133–144) and (Bradford, 1986 *HortScience* 21:1105–1112).

In seed priming, the seeds are placed in an aerated osmotic media of known water potential. In this process, the osmotic solutions induce a water potential that prevents the completion of germination (radicle emergence). Seeds are, however, able to imbibe and complete the early phases of germination under limiting water content conditions. The duration of the priming treatment has been reported to be from less than 24 hours (Guedes and Cantliffe, 1980, *J. Amer. Soc. Hort. Sci.* 105:777–781) to several weeks (Khan, et al., 1980/81, supra) and is dependent on species, cultivar and even seedlot. Seeds are then dried back. After priming, seeds can be sown with existing planters. Results obtained from priming different crop seeds have been reviewed by Bradford, 1986, supra. In general, seedling emergence of primed seeds is earlier and more sychronous than dry sown seeds. Improvements in plant growth and yield characteristics have also been documented.

In the prior art priming processes, several different osmoticums have been used to achieve the water potential for priming including high molecular weight (MW of 6000–8000) polyethylene glycol (PEG) and/or inorganic salts (Heydecker and Coolbear, 1977, supra). After priming, the seeds are removed from the solution used for establishing the water potential before being dried back.

Several technical and logistical difficulties have been encountered with the prior art priming techniques. For example, osmotic solutions require continuous aeration and in general, a large volume of priming solution is required per quantity of seeds. Reductions in percentage seedling emergence have been reported with the use of inorganic salts (Brocklehurst and Dearman, 1984, *Ann. Applied Biol.* 102:585–593). A relatively high concentration of PEG in solution is viscous and has low oxygen solutibility and diffusivity (Mexal, et al., 1975, *Plant Physiol.* 55:20–24).

An alternative to the use of solutions is to prime seeds in a solid medium. A solid material should have a high water holding capacity and allow seeds to imbibe. Peterson (1976, *Sci. Hort.* 5: 207–214) described a procedure to prime onion seeds in a slurry of PEG 6000 and vermiculite. A ratio of three to four parts vermiculite moistened with PEG solution were mixed with one part seed. Although this technique overcame the need for aeration, he reported that the seeds were difficult to separate from the vermiculite. Methods have been described to increase the seed moisture content of large-seeded vegetables prior to sowing (Bennett and Waters, 1984, *J. Amer. Soc. Hort. Sci.* 109:623–626 and 1987, *J. Amer. Soc. Hort. Sci.*, 112:45–49). Seed moisture content of lima beans (*Phaseolus lunatus*) and sweet corn (*Zea Mays*) was increased by combining seed, vermiculite and a known amount of water in a closed container. This mixture was incubated and then the vermiculite sieved away prior to sowing the hydrated seed. Seedling establishment was improved by the pre-sowing treatments for both crops.

Inoculation of seeds with bacteria or chemicals prior to planting is known in the art. For example, United Kingdom patent specification 849,210 discloses inoculating seeds under reduced pressure to enable penetration of the bacteria under the coat of the seed and thus survival of the bacteria for a period of time. This procedure is expensive and appears to be limited in the range of bacteria that can be inoculated into seeds.

SUMMARY OF THE INVENTION

Accordingly, it is an object of the invention to provide a novel technique for priming seeds.

It is a still further object of the invention to provide a novel technique for inoculating seeds.

It is a still further object of the invention to provide a novel technique for inoculating soil.

It is a still further object of the invention to provide a novel technique for inoculating soil for bioremedial purposes.

In accordance with the above and further objects of the invention, a solid phase media is used to prime seeds. The solid phase media includes a solid matrix that provides a structure to hold water and allow gas exchange. Chemical treatment and addition of microorganisms may be accomplished during priming. The seeds may be used to inoculate soil with bacteria such as for example, bacteria useful in agriculture or to breakdown contaminants in the soil and facilitate plant uptake of contaminants from soils, such as for example, radionuclides.

The solid matrix holds water with an appropriate water potential to initiate and maintain metabolism prior to germination. The temperature and aeration are at a level that reduces damage.

The seeds are then dried back and the drying back may be performed in more than one phase with aeration and moisture control interrupting the drying operation to promote healing. In one embodiment, the seeds are separated from the matrix after being dried although, in other embodiments, the seed in the matrix may be used for planting, particularly in the case of small seeds which require added matrix material for efficient use in planters or in the case where the matrix aids in the development of beneficial microbes or the beneficial application of chemicals to the seed.

From the above description, it can be understood that the method, matrix and seed of this invention have several advantages such as: (1) there is a synergistic relationship with inoculation by microorganisms or the use of chemical treatment in the priming; (2) superior synchrony of emergence and speed of germination are provided; (3) a higher yield is obtained from the seeds; and (4) the priming provides a certain measure of synchronism with other techniques such as the coating of seeds for protection.

SUMMARY OF THE DRAWINGS

The above noted and other features of the invention will be better understood from the following detailed description when considered with reference to the accompanying drawings in which:

FIG. 8 is a diagrammatic view of a separator assembly according to the invention.

DETAILED DESCRIPTION

Figure 1:
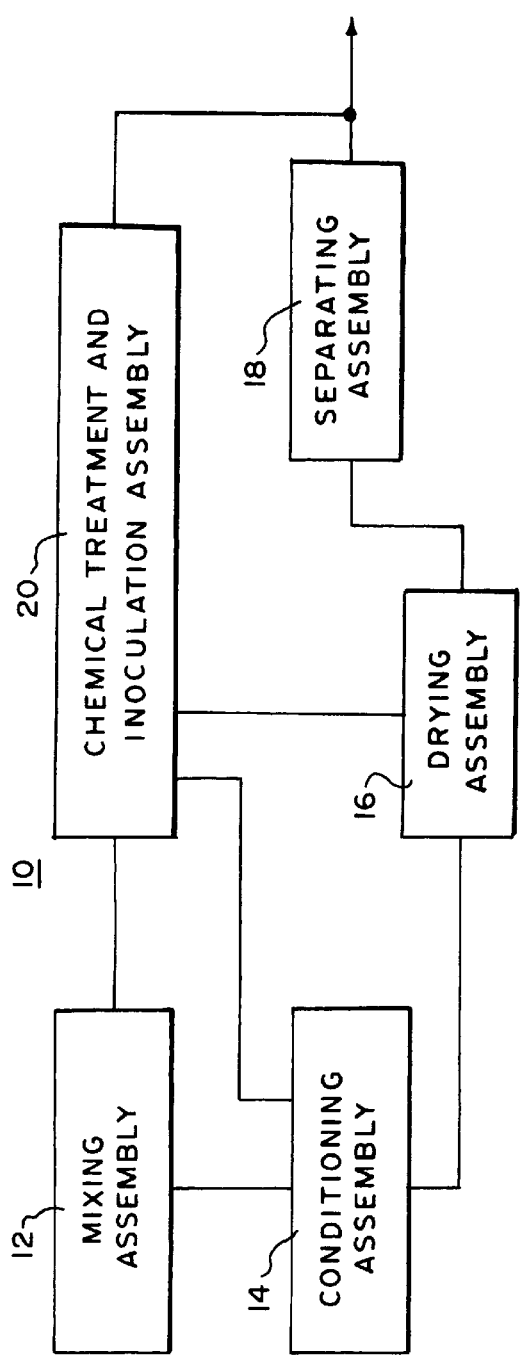
FIG. 1 is a block diagram of a priming system in accordance with an embodiment of the invention.

To prime seeds, the seeds are incorporated in a solid phase matrix comprising finely divided nonpathogenic, water-holding solids. Preferably, the matrix material, not including the seeds, is in such proportion and distribution with respect to the seeds so that the seed surfaces are sufficiently aerobic to favor aerobic metabolism of the seeds and of beneficial microorganisms, to deter the growth of unfavorable faculative anaerobes or anaerobic microorganisms and to permit proper metabolic changes. In most cases, this is accomplished by using the proper volumetric ratio of seed to matrix material and aeration.

The volumetric ratio of seed to matrix material should be for practical reasons in the range of one volume of seed to 120 of matrix material at one extreme to one of matrix to ten of seed at the other extreme. Preferably, a one to one ratio of seed to matrix is generlly favorable but the ratio may be lower as in cases where seed exudation and germination inhibitor removal are significant seed priming and treatment objectives and higher such as when microbial inoculation calls for retaining exudates. In cases where the seed to matrix mixture contains a substantially larger volumetric ratio of seed over matrix, proper aeration during priming can be maintained through a combination of mechanical mixing and aeration of the seed plus matrix mass or more aeration.

The matrix material, when containing the water necessary to prime the seeds in question, should be sufficiently friable, nonclumping etc. so that, when desired, it can be separated from the treated seeds after treatment without damage to the seeds. The particle size of the matrix material is not unduly critical as long as surface area is adequate, but for mechanical reasons should be smaller or larger than the seed being treated, usually less than 20 mesh and preferably substantially different. Typically, a material less than about 60 mesh is preferred; for example the Agro-Lig described hereinafter was 90%/wt less than 200 mesh, the soft coal was less than 60 mesh.

One type of matrix is formed of organic solids, for example a carbonaceous, preferably a lignateous solid which has a large equilibrium water potential and preferably has an osmotic potential component which is at least about 90% and preferably greater than 95% of the total water potential, measured as described below. Examples of such material include coal, especially soft coal, lignateous shales such as the leonardite shale, sold as Agro-Lig, and sphagnum moss.

Another type of matrix material is inorganic such as calcined clay mineral, vermiculite and perlite. To achieve a practical cost-effective system using an inorganic particulate matter as the matrix, the bulk density of a matrix of that inorganic particulate matter is preferably above 0.3 grams per cubic centimeter. In this specification, bulk density means the weight in grams of a given volume of particulate material divided by its volumes in cubic centimeters. When using inorganic materials, the water potential is generally determined not primarily by osmotic potential but primarily by matric potential.

In the process of the invention, the seed to be treated, a predetermined amount of solid matrix material and a predetermined amount of water are admixed and the mixture allowed to equilibrate, preferably in a container designed to provide aeration but which reduces evaporative losses, for example, a closed metal container or bag, for a time and at a temperature sufficient to allow the seeds to imbibe water from the matrix and maintain or change a prescribed water content equilibrium temperature and aeration sufficient to enhance resultant plant vigor, i.e., enhance emergence, growth or yield characteristics, but short of that which would cause the seed to sprout. Particularly useful materials for the matrix are coal related materials, calcined clay, diatomaceous earth vermiculite, sawdust, perlite, peat/moss, corn cobs and grain dust.

As in solution priming, the equilibrium amount of water for the system to prime the seed is dependent on the specific seed variety, its state or condition, and the water potential of the solid matrix material. Typically the solid matrix material should have a water potential between about −0.5 to about −0.2 megapascals at equilibrium with the seeds. With control of temperature, this range may be extended to −0.2 to about −3.6. The exact conditions depend on the objectives and species such as destruction of inhibitors or physiological or physical blockages. The seed priming art to some extent is still empirical, and while typical water amounts and media water potentials for given seed types are already generally known from the solution priming art and solid state matrix priming experiments for some seeds, it is frequently best to test a small sample of a new seed over a readily determined range of water potentials and temperatures to determine what conditions of temperature, water potential and time cause appropriate imbibing of water by the seed and resultant pregermination events. After this priming, the seeds may be dried to a resting or dry storage state, with or without the matrix material. Treatment with beneficial microbes or chemical treatment may be before, during or after priming.

In one process of the invention, a known weight of seed is wet with about 25% by weight of water. The total water utilized is typically in the order of about one liter per kilogram of seed but varies with seed size and seed condition. The seed is mixed with the dry, flowable, particulate solid matrix material and water with appropriate chemicals or biologicals added so as to wet seeds and particulate matrix material uniformly. After the predetermined amount of water for priming is admixed with the coated seeds, the mixture is held at a predetermined temperature for a time sufficient to allow the seeds to maintain a desired moisture content equilibrium, usually one to about fourteen days. In other processes, the water, seed and matrix material are mixed in a continuous flow or batching blending system. The ratio of water may also vary substantially from 25 percent of the seed weight.

The seeds that can be treated can be virtually any seed, including most vegetable crops, ornamentals and agronomic crops. Included are cucumber, lettuce, carrot, onion, melons, sweet corn, tomatoes, eggplant, peppers, bean radish, squash, pea, flower seeds, alfalfa and soybean. Several different apparatus can be used for these procedures. One such apparatus is described below.

In FIG. 1, there is shown a block diagram of a priming system 10 having a mixing assembly 12, a conditioning assembly 14, a drying assembly 16, a separating assembly 18 and a chemical treatment and inoculation assembly 20. In this system, seeds and a matrix are: (1) mixed together either with no chemical treatment or inoculation of the seeds or with chemical treatment and/or inoculation of the seeds; (2) conditioned; (3) dried back; and (4) in some embodiments, the matrix medium and seeds are separated.

The chemical treatment or inoculation generally takes place in the chemical treatment and inoculation assembly 20 which may communicate with the mixing assembly 12, the conditioning assembly 14, the drying assembly 26 or the separating assembly 18 or none of them. The mixed matrix, seeds and water are utilized for pre-germination metabolism, after which the seeds may be dried back in the drying assembly 16 although from time to time the drying assembly 16 and and conditioning assembly 14 are used intermittently for staged conditioning and drying. The drying assembly 16 may communicate with the separating assembly 18 to separate the matrix from the seed in some embodiments although such separation is not always required. The treated seeds may be stored and used later or immediately utilized.

Not all seeds are subject to chemical treatment or inoculation, and thus, the chemical treatment and inoculation assembly 20 is not always used. However, in some embodiments, the seeds may be chemically treated or inoculated with microbes prior to being mixed in the mixing assembly 12 with water and matrix, or in the alternative, such treatment may be applied in the conditioning assembly 14, the drying assembly 16 or later after preconditioning.

In some embodiments, the beginning stages of metabolism occur until the beginning of germination as indicated by the emergence from the seed hull of embryo, at which time inoculation with beneficial microbes takes place. After the inoculation, the seeds may be returned to the conditioning assembly 14 for healing to be restored to a pre-germination stage without full germination and be dried back for later use.

Figure 2:
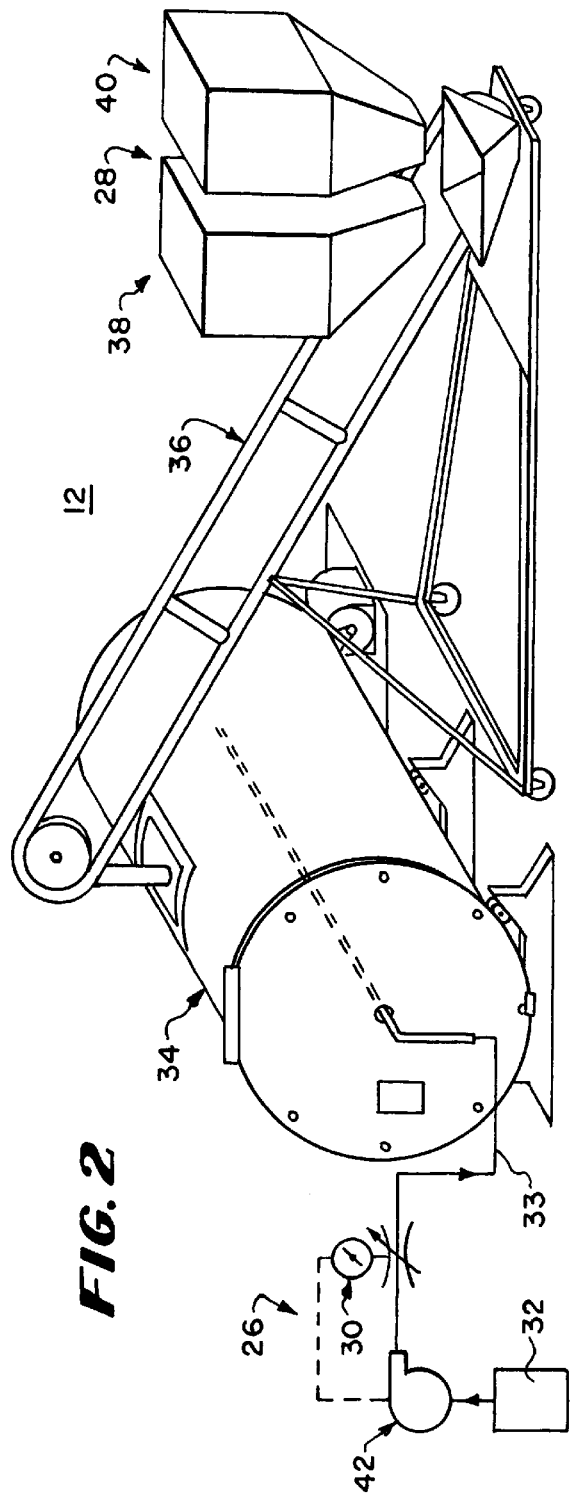
FIG. 2 is a diagrammatic view of a portion of a mixing system used in the embodiment of FIG. 1.

In FIG. 2, there is shown a schematic view of a mixing assembly 12 having as its principal parts a water source 26, a solid matter source 28 and a rotatable mixing tank 34 connected together so that the source of water or water plus additives such as potassium nitrate and the solid matter source 28 such as matrix material and seeds communicate with a rotatable mixing tank 34 which combines the ingredients into the proper mixture for oxidation, temperature control and water potential control. All of these sources may pre-mix the solid matter and moisture and then apply it to the mixing tank or they may be individually applied or combined to pairs and applied or combined with treatment material or the chemical treatment material may be applied to any of the ingredients such as the source of water or the source of matrix or to the seeds alone.

The source of water 26 includes a meter 30, a source of water 32, and in some embodiments a pump 42 connected together so that a metered amount of moisture may be applied to a mixing mechanism, which in the embodiment of FIG. 2, is a rotatable tank. It is adapted to receive the water and solid matter and then to be rotated for thorough mixing. Of course, other embodiments may be utilized such as a tank with internal stirring means rather than a rotating tank and/or connections with rotatable universal joints that rotate with the rank rather than connectors at the center of rotation.

The solid matter source 28 includes a seed and solid matrix conveyor 36, a source of seeds 38, and a source of matrix material such as clay 40. These ingredients may be premixed or moved one-by-one into the tank 34 by an auger or forced air flow or gravity or any other means.

Figure 3:
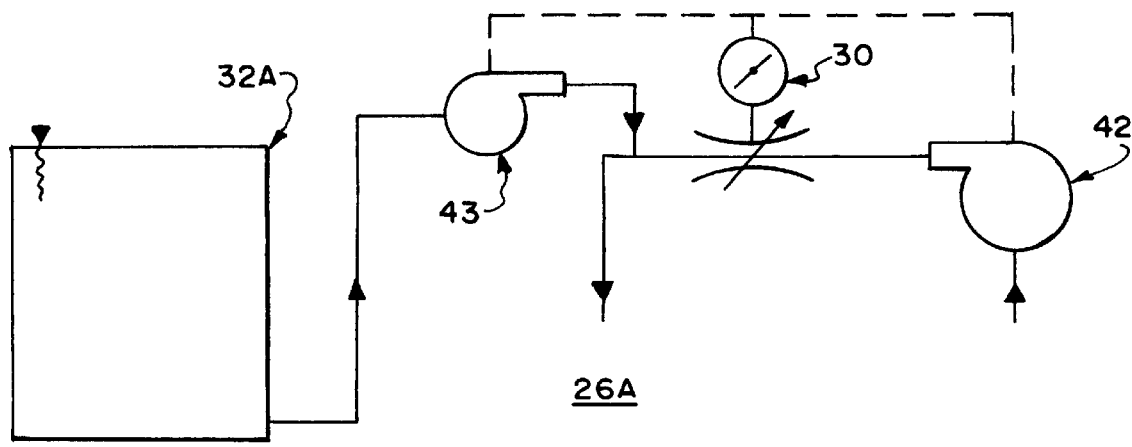
FIG. 3 is a diagrammatic view of another embodiment of mixing system used in accordance with the embodiment of FIG. 1 instead of using the embodiment of FIG. 2.

In FIG. 3, there is shown an embodiment of water source 26A having a tank of water 32A which contains water and potassium nitrate. The tank communicates with a pump 42 and a meter 30 in a conduit 31 for supplying a mixture of liquid ingredients which may include additives such as potassium nitrate to condition for light sensitivity or chemicals beneficial to seed treatment or being antifungal or antimicrobial or with beneficial microbials for inoculation and in some embodiments, nutrients therefore.

With this arrangement, a carefully metered amount of water may be supplied to provide the correct matrix potential. In some applications, a small amount of water is supplied and then the supply is disconnected from the tank which is rotated for mixing and then further water is supplied. The intermittent stationary portions of the tank may be utilized to also add more dry matter if desirable so that the mixing together may proceed with stepped amounts of dry matter and water.

Figure 4:
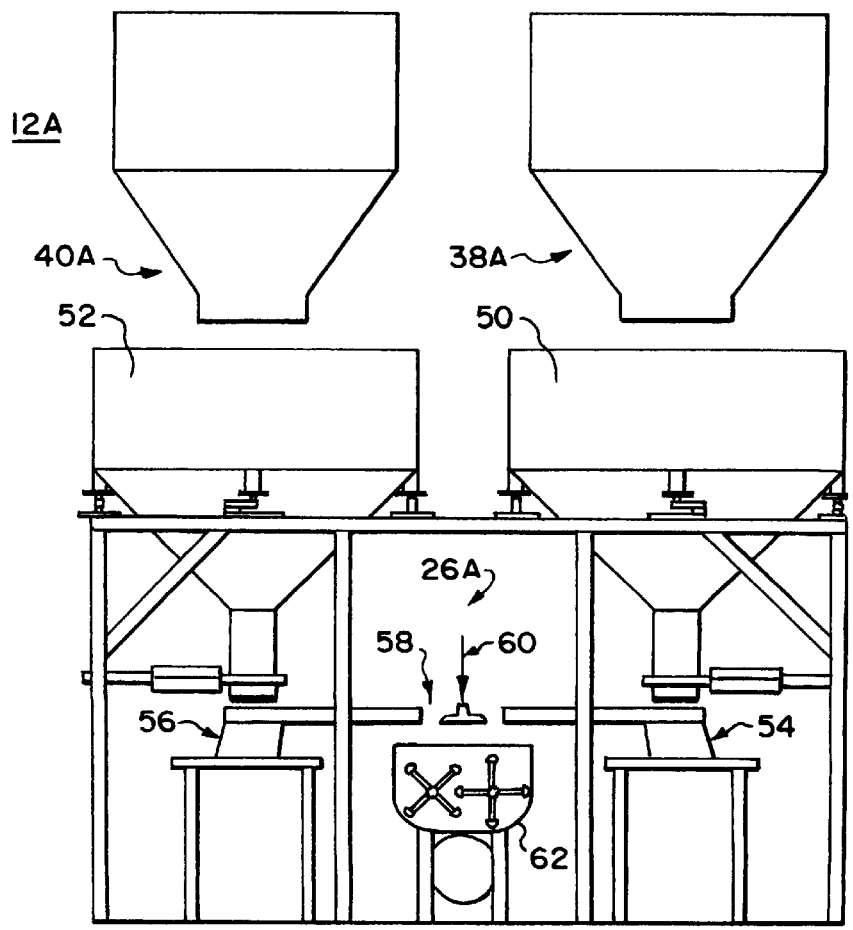
FIG. 4 is a diagrammatic view of a conditioning system used in an embodiment of a portion of FIG. 1.

In FIG. 4, there is shown a schematic diagram of another embodiment of mixing assembly 12A having a source of seeds 38A, a source of dry matter 40A, the source of water and liquid additives 26A, a mixing section 58, and a mixture agitator and transporter 62. The source of seeds 38A and the source of dry matter 40A each include a different one of the hoppers 50 and 52 respectively for containing bulk seed and dry matter such as matrix. At the bottom end of each, there is a corresponding one of the seed conveyors 54 and conveyor 56 which are aligned directly in the line of gravity underneath the seed and matrix hoppers 50 and 52 respectively and are drivable at controlled speeds independently to transport from the hoppers controlled amounts of material for mixing in the mixing station 58.

The bottoms of the hoppers are adjustable and the speed of the containers are adjustable so that the ratio of mixing may be proportional in accordance with the type of seed and the type of matrix material. Similarly, the water supply 26A supplies water at a controlled rate through a conduit 60 into the mixing station 58 so that controlled amounts of matrix material, seed and water or water solutions are mixed together at the mixing station 58 in a continuous process for thorough mixing with the station 58 receiving at any one time between 1 percent and 60 percent of the total amount a batch to be processed during batch processing, or if continuous processing is used, a volume of properly proportioned materials which is adapted to fit into a flow stream no faster than the slowest processing of that stream. The proportional mixtures are mixed at the station 58 and conveyed by the mixer, agitator and transporting system 62 which moves the mixture along by a series of panels to an outlet where it may be conveyed to the seed conditioner. The seed conditioner may accumulate it batch by batch for processing or the seeds may be conditioned in a continuous process.

Figure 5:
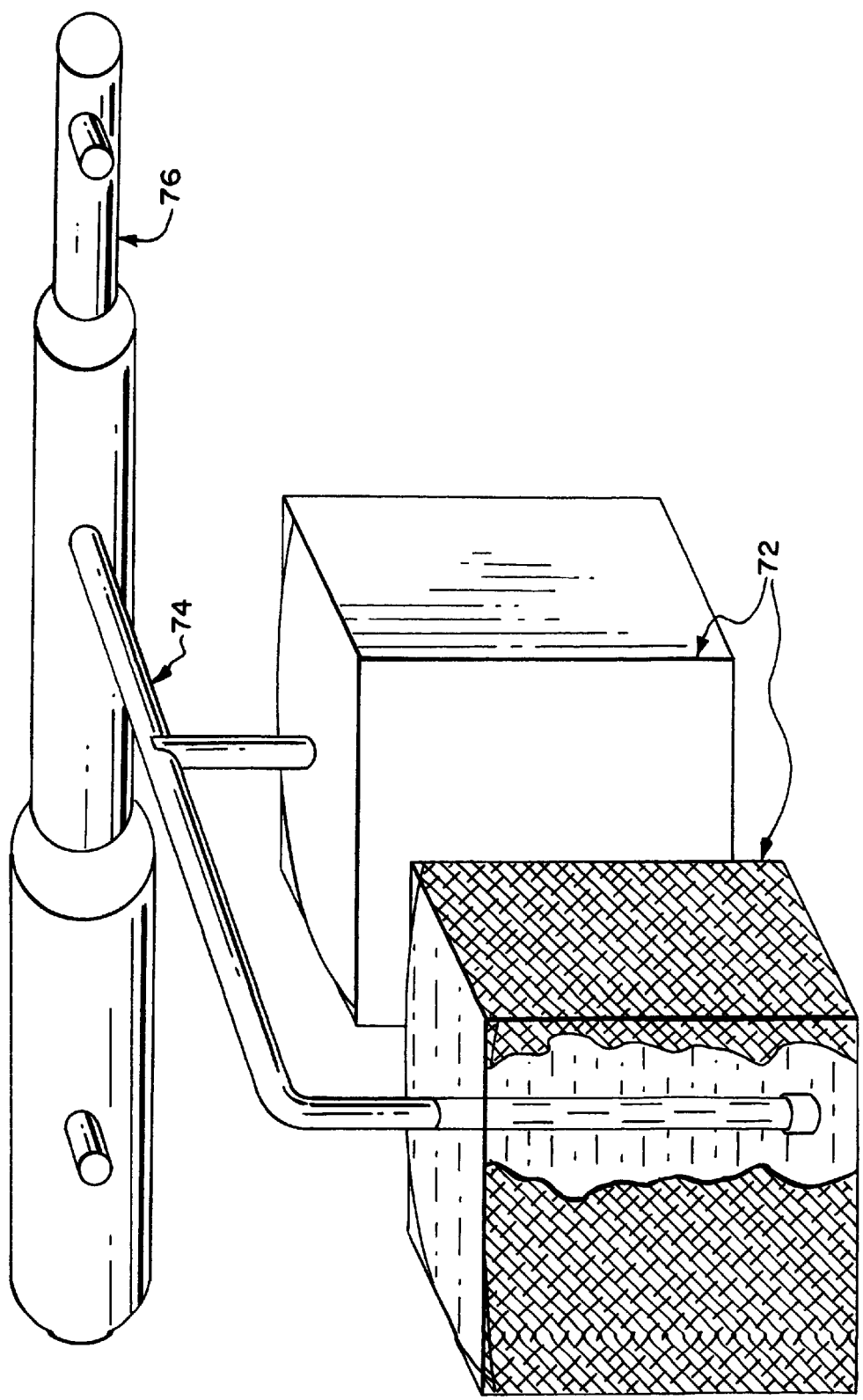
FIG. 5 is a diagrammatic view of a drying system used in accordance with the embodiment of FIG. 1.

In FIG. 5, there is shown a conditioner 14 which includes a means for controlling the temperature, moisture and oxygen supply of the matrix containing seeds to promote pre-germination conditioning. In the embodiment of FIG. 5, all of these functions are performed in a unitary manner by a porous fabric bag 72 which contains the matrix and seeds, a suction manifold 74 positioned for even moisture and temperature drawing of air through the fabric bag 72 and matrix to a vacuum manifold 76 and a temperature and moisture controlled room for this processing. For very small amounts, the air drawing supply 74 is unnecessary since there will be adequate natural transfer of heat and oxygen through the matrix material for the desired purposes.

The fabric bag 72 has a open end for supplying the mixture to the bag and an openable bottom end for supplying conditioned seeds to a transport conveyor 80 after a conditioning stage. In practice, the seeds may be conditioned in the fabric bag 72 and then transported for drying back through a 10 percent stage of drying and then returned to the bag for further conditioning. Moreover, the conditioning may extend until the beginning of emergence and inoculated and dried and conditioned again prior to emergence.

To draw air through the fabric bag 72, a centrally located vacuum pipe 74 extends downwardly. It is designed so that the larger surface area on the outside of the fabric bag 72 pulls cool dry air through the wider area, and as it picks up some heat and moisture, the rate of flow becomes greater since it is moving inwardly through spheres of smaller area to maintain uniformity of temperature through the bag and relative uniformity removal of moisture. In the preferred embodiment, the bags generally contain between 20 pounds and 1,000 pounds of mixture, contained in a room that is between 10 degrees Centigrade and 15 degrees Centigrade with air being pulled from a manifold under a vacuum pressure of a negative 10 pascals through an outer surface area of 75 square feet to an inner perforated conduit having a diameter of between 1 inch and 15 inches and open pores and ends for drawing air having a combined area of 75 square centimeters.

After a conditioning stage, the fabric bags 72 may be physically moved to driers and dumped into the driers in a manner shown herein or the bottoms may be opened and conveyor mechanisms 80 may convey the mixture to driers or to a drying stage.

Figure 6:
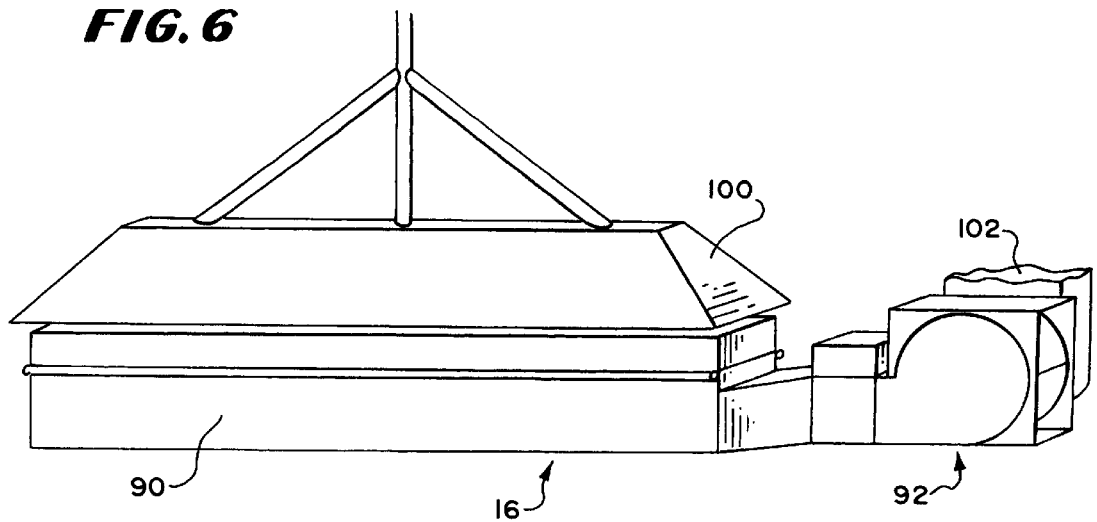
FIG. 6 is a diagrammatic view of another embodiment of drying system in accordance with the invention.

In FIG. 6, there is shown one embodiment of drying assembly 16 having a bin assembly 90, a blower assembly 92, and in some embodiments a cover assembly 100. A source of air pressure 102 applies air through blowers or the like to the blower assembly beneath the bin assembly 90. The bin assembly 90 has a fabric bottom through which the air pressure blows to cause turbulence in the matrix material spread across the bin assembly 90 for drying thereof by air flow. A cover may be placed over the bin assembly 90 to create slight negative pressure if desired for dust control and moisture may be extracted by recirculation of the air through desiccators in the cover.

In one embodiment, air pressure in the manifold beneath the bin assembly 90 of a positive 50 pounds per square inch is applied through a 60 gauge fabric for drying matrix material applied in a layer between 4 inches and 3 feet deep and having a pressure on the fabric of between 6 ounces and 15 pounds per square inch.

Figure 7:
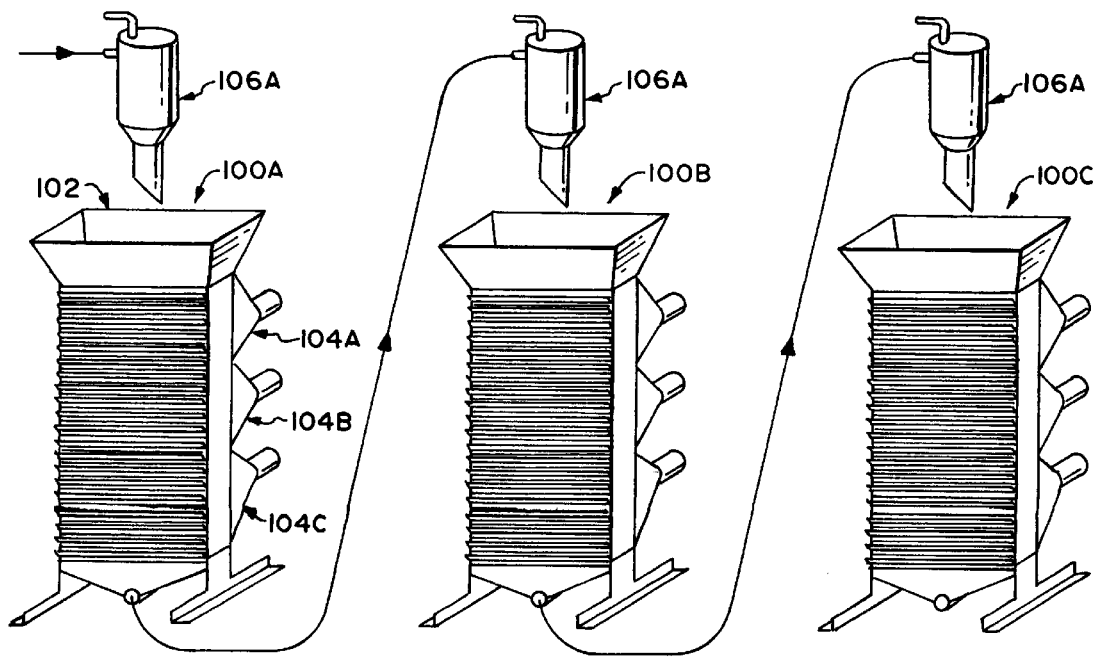
FIG. 7 is a diagrammatic view of still another embodiment of drying system used with the invention.

In FIG. 7, there is shown another embodiment of drying assembly having a plurality of drying towers 100A, 100B, and 100C each of which receives a mixture of matrix and seed for drying with the seed being applied to the top of the tower 100A through a conveyor 106A which may be an auger or an air blower or the like for filling the tower 100A. The tower 100A is emptied into the tower 100B through a similar conveyor 106A and so on down the line until the drying operation is completed, after which the mixture may be moved to a separator for sifting and separating or may be stored for use in a planter with the matrix material and seed combined or moved to a location for chemical treatment or biological inoculation. Each of the towers is identical and so only the tower 100C will be described.

To provide a stage of drying, the drying tower 100C contains an elevated bin 102 having a plurality of stages of air flow conduits 104A, 104B and 104C. Any number of such stages may be supplied and they include within them a blower for blowing air crosswise through the tower where it is received by the next section for blowing crosswise again through the tower from the opposite side forwardly so that the air blows across the tower through several stages, three being shown for illustration in FIG. 7. A desiccant or other dryer may be utilized at each stage to remove moisture from the air as it dries the mixing combination.

In FIG. 8, there is shown one embodiment of separator for separating the matrix material from the seed. This embodiment includes commercial sifters with gauge shifting designed to hold the seed but permit the matrix to fall through or to hold the matrix and permit the seed to fall through or to sort the seed and matrix at two different slides or conveyors for convenient separation.

With this arrangement, seeds are primed using a solid phase matrix, rather than using aqueous solutions. The matrix comprises finely divided non-plant-pathogenic, water-holding solids. Preferably, the matrix material, not including the seeds, is in such proportion and distribution with respect to the seeds so that the seed surfaces are sufficiently aerobic to: (1) favor aerobic metabolism of the seed and of beneficial microorganisms; (2) deter the growth of unfavorable facultative anaerobes or anaerobic microorganisms; and (3) to permit proper metabolitic changes. In most cases, this is accomplished by using the proper volumetric ratio of seed to matrix material and aeration.

A slight modification of this equipment permits the screening out of bad seeds. In this method, higher gravity or larger seed particles are eliminated by screens or agitating until the larger seed particles are removed. In this specification "seed particles" means the seed and material adhered to the seed by sticking to seed exudate. This process is a result of noticing that injured seeds exude more than healthy seeds and thus more matrix material or the like stick to them.

The solid matrix priming compositions described above can also advantageously contain: (1) prescribed amounts of known seed fungicides such as thiram, captan, metalaxyl, pentachloronitrobenzene, and fenaminosulf, so that the finished primed seed is coated with or absorbs the desired amount of fungicide, such as is known to those skilled in the art; (2) microorganisms useful to the crop such as those useful in crop protection, stimulation or establishment, and for such purposes, some significant bacteria are strains of: *Bacillus enterobacter*, Pseudomonas, Rhizobia and Serratia species and some significant fungi are strains of Trichoderma, Gliocladium and Laetisaria species; (3) pesticides such as fungicides or bactericides included prior to, during or after the solid matrix priming; and (4) growth regulators such as potassium nitrate, gibberellic acid, DCPTA, ethephon.

In this specification, "solid matrix priming" is considered the process whereby seeds are intimately mixed with particulate solid phase media in the presence of sufficient water to realize a moisture content in the seed which allows for germination processes to occur but which prevents radicle emergence. During priming and especially during solid state priming, the addition of chemical additives and microorganisms is especially beneficial. In this specification, the language "added beneficial microorganisms" means a beneficial microorganism that is added to the composition at a level in excess of that naturally occurring on the seed being primed.

In this specification: (1) threshold germination temperature range means that range of temperatures for a certain species within which seeds of that species will germinate at a predetermined moisture level and with adequate oxygen; and (2) threshold germination moisture range means that range of moistures for a certain species within which seeds of the species will germinate at a given temperature and with adequate oxygen.

In addition to the above ranges, the limiting points of moisture and temperature in this specification are defined as follows: (1) threshold germination temperature base means that temperature below which a seed for a given species will not germinate even though the oxygen and moisture levels are acceptable; (2) threshold germination critical maximum temperature means that temperature above which a seed of a given species will not germinate even though there is an acceptable moisture level and adequate oxygen; (3) threshold germination moisture base means that moisture level below which a seed of a given species will not germinate even though the temperature and oxygen are appropriate; and (4) threshold germination moisture critical maximum level means that moisture level in soil above which a seed of a given species will not germinate even though the temperature and oxygen are adequate.

Other convenient terms are defined as follows: (1) emergence rate index means the sum of the emerged seeds, n, on each day multiplied by a quantity for that day, quantity for that day being equal to the total number, c, of days in the assay minus the count, n, of seedlings on that day; and (2) synchronization factor means the emergence rate index that occurs in the period that is one-quarter of the time into the total assay period. The assay period is a normal field crop emergence period. The emergence rate index and synchronization factor can be calculated using seeds germinated instead of seedlings emerged to arrive at a similar number. This may be called a germination rate index.

The above values are determined empirically for a given seed and variety and may be used in planting.

A sufficient amount of matrix or a matrix of material sufficiently adsorbent or absorbent to remove enough inhibitors to prevent delay of more than fifteen percent of the time duration of activation prior to a control time of germination in which the inhibitor is substantially completely removed by an appropriate washing technique is required. The time of germination in this specification is that the visible radicle protrusion can be observed and the activation period occurs when membranes become differentially permeable and conversion occurs from substantially passive solute transport in and from the seed. The amount and type of matrix is also selected to either retain or permanently remove exudates so that: (1) in the case of removal, it is not deleterious such as for example, to encourage pathogen growth; or (2) in the case of retention, to enable growth of innoculated beneficial microbes on seeds.

The matrix priming process also provides a superior approach to SAR (Systemic Acquired Resistance) as described in "Systemic Acquired Resistance" by Scott Uknes, et al., in *Hort Science*, Vol. 30(5), August, 1995, pages 962 and 963 and other publications. For example, using this process, additives may be mixed with the seeds during conditioning described above to induce immunity. Both pathogens and non-pathogens are able to induce immunity. Moreover, the known seed fungicides described above such as thiram, captan, metalaxyl, pentachloronitrobenzene, fenaminosulf and some growth regulators including those mentioned above may have this effect. Systemic acquired resistance is aided by the conditioning described herein, particularly when the matrix includes lignin. The priming process stimulates certain genes that cause resistance to pathogens. This is sometimes referred to in the literature as a "signal" that permits the induced immunity to some pathogens that are present at the time of the signal.

EXAMPLE

Seed-Solid Matrix—Water

Preliminary studies were conducted to determine the ratio of seed to solid matrix to water for effective solid matrix priming (SMP). The goal was to achieve a seed moisture content that would allow favorable pregermination activity and prevent radicle emergence for a particular crop. This optimal ratio was determined on an empirical basis by mixing seed and solid matrix on a weight to weight basis. The water was calculated as a percentage of the seed and solid matrix by weight. The seed, solid matrix and water were mixed and incubated at 15 degrees Celsius in a closed

TABLE 1

The optimal ratio of seed-solid matrix for effective priming of different vegetable at 15 degrees Celcius.
PARTS BY WEIGHT

| Solid Duration Crop (day) | Matrix | Seed | Solid % (z) Matrix | Water |
|---|---|---|---|---|
| Tomato | | | | |
| Agro-Lig(1) | 1.0 | 1.5 | 95 | 6 |
| Soft coal(2) | 1.0 | 1.5 | 95 | 6 |
| Sphagnum moss | 1.0 | 1.5 | 90 | 6 |
| Carrot Agro-Lig | 1.0 | 1.5 | 90 | 6 |
| Onion Agro-Lig | 1.0 | 2.0 | 80 | 6 |
| Lettuce Agro-Lig | 1.0 | 2.0 | 85 | 1 |
| Cucumber Agro-Lig | 1.0 | 1.5 | 60 | 6 |

(z) Percentage water based on dry weight of solid matrix
(1) Total % organic 84%, less than 1% nitrogen
(2) Total % organic 90%, less than 1% nitrogen container with a small hole in the lid for ventilation. Results are shown for different crops in Table 1.

Moisture Contents and Water Relations of Humates and Seeds

Seeds of the five crops were primed in Agro-Lig as described in Table 1. Seeds were separated from the Agro-Lig by shaking through appropriate sized sieves. At the end of the priming treatment, the percent moisture content of the seeds in Agro-Lig was determined gravimetrically. The matrix potential (psi-m) of Agro-Lig was determined as described by Black (ed.), 1965, "Methods of Soil Analysis" Academic Press, New York, N.Y. The osmotic potential (psi-s) of the Agro-Lig was determined by the following procedure. Four parts distilled water was added to one part Agro-Lig (wt/wt), samples from each crop to produce an extract (Greweling and Peech, 1960, N.Y. Agri. Expt. Station Bul. 960).

The liquid phase was filtered and the psi-s of the Agro-Lig solution extract was determined with a Microsmettte model 5004 (Precision Systems Inc., Natick, Mass.). The psi-s of Agro-Lig without seeds was also calculated to quantify the influence of seed leakage on the psi-s of the medium. The total water potential of the Agro-Lig was determined for each crop after SMP with a HR-33 dewpoint microvolt meter and C-52 sample chamber (Wescor Inc., Logan, Utah). Thus the total water potential calculated from its component fractions, psi-m and psi-s could be compared with the water potential measured by thermocouple psychrometry. There were four replications per treatment for each study.

Seedling Emergence Studies

The influence of solid matrix priming (SMP) and other conventional seed priming treatments was studied on seedling emergence and plant growth in growth chamber studies. SMP of tomato (*Lycopersicon esculentum*) 'New Yorker' was conducted with Agro-Lig, soft coal and sphagnum moss (Table 1). Other priming treatments included: −1.0 MPa PEG 8000 (Coolbear, et al., 1980, *Seed Sci. and Technology* 8:289–303) and 1.0% $KNO_3$ and 1.5% $K_3PO_4$ (Ells, 1963, *Proc. Amer. Soc. Hort. Sci.* 83:684–687). SMP of carrot (*Daucus carota*) 'Danvers 126' was conducted with Agro-Lig (Table 1). Other priming treatments included: 25% PEG 8000 (Szafirowska, et al., 1981, *Agron. J.* 73:845–848) and 0.2 m $KNO_3$+0.1 m $K_3PO_4$ (Haigh, et al., 1986, *J. Amer. Soc. Hort. Sci.* 111:660–665). SMP of onion (*Allium cena*) 'Downing Yellow Globe' was performed with Agro-Lig (Table 1). Other priming treatments included: 34.2% PEG 8000 (Brocklehurst and Dearman, 1983, supra) and 0.2 m $KNO_3$ 0.1 m $K_3PO_4$ (Haigh, et al., 1986 (supra).

All priming treatments were performed at 15° C. for 6 days which, in many cases, is a modification of the original procedure described in the literature. All priming treatments were prepared with 0.2% (wt/v) thiram (Gustafson, Inc., Dallas, Tex.) as a fungicide.

Seeds were rinsed and blotted dry after priming. Seeds were sown in flats filled with an artificial (Peat-vermiculite) soil media. There were four replications of 50 seeds per rep in a randomized complete block design. Flats were maintained in growth chambers with 20° C. day and 10° C. night with a 12 hour photoperiod. Seedling emergence was recorded daily and the plant dry weight was determined at the termination of the emergence period.

Thermodormancy

Alleviation of thermodormancy by priming was studied in lettuce (*Lactuca sativa*) 'Montello'. SMP of lettuce was performed with Agro-Lig (Table 1). Conventional priming treatments included: −1.5 MPa PEG 8000 (Bradford, 1986, supra) and 1.0% $K_3PO_4$ (Cantliffe, et al., 1984, *Plant Physiol.* 75:290–294). After priming, seeds were rinsed and allowed to dry. Seeds were placed to germinate on moistened blotters in closed containers. The containers were maintained at a constant 35° C. in the dark. There were four replications of 50 seeds each and the percent germination was determined after 10 days.

SUMMARY

Seed-Solid Matrix—Water

The solid matrix served as a reservoir for water and 1.5 to 2.0 parts of solid matrix were required per part of seed to allow effective priming (Table 1). The percentage of water added varied with crop and ranged from 60 to 95%. Despite the high initial water content of the mixture, the solid matrix remained friable and did not lose its structure.

Moisture Contents and Water Relations

Seeds of all crops were able to imbibe water from the Agro-Lig since a reduction in the Agro-Lig moisture content was measured after SMP (Table 1 and 2). At equilibrium all crops except for cucumber had a higher percentage moisture content than the Agro-Lig (Table 2). The treshold seed moisture content for priming varied with crop and ranged from 42 to 24 percent (wet basis).

The components of the total water potential responsible for priming were determined. The water potential of Agro-Lig is the sum of the psi-s and psi-m. The water potential of the medium varied with crop and ranged from −1.34 MPa for SMP tomato to −1.77 MPa for SMP cucumber. The psi-m contributed only a small fraction of the total water potential and ranged from 3 kPa for SMP tomato to 23 kPa for SMP cucumber. The psi-s due to the Agro-Lig alone was responsible for the largest portion of the water potential, however, additional osmotic effects was attributed to solute leakage from seeds into the medium. Calculation of the Agro-Lig water potention by its component parts overestimated (predicted a lower water potential than) the Agro-Lig, except in the case of the cucumber, as determined by thermoocouple pychrometry (Table 2).

Seedling Emergence Studies

Sowing tomato seeds from all priming treatments decreased the time to 50% seedling emergence (T50) and increased the plant dry weight compared to the non-primed control (Table 3). SMP with Agro-Lig and priming with PEG resulted in greater percent emergence, however, the PEG treatment had a higher T50 and less dry weight per plant compared to other priming treatments. From this study and other experiments (data not shown), Agro-Lig was chosen for the solid medium for the bulk of the studies.

TABLE 2

The percent moisture content of Agro-Lig and seeds after SMP. The total water potential of the Agro-Lig was determined by thermocouple pychrometry.

| Crop | PERCENT MOISTURE CONTENT | | | Psi MPa |
| --- | --- | --- | --- | --- |
| | Agro-Lig (dry basis) | Seed (dry basis) | Seed (wet basis) | |
| Tomato | 50 | 61 | 38 | −1.1 |
| Carrot | 42 | 67 | 40 | −1.2 |
| Onion | 38 | 73 | 42 | −1.4 |
| Lettuce | 42 | 72 | 42 | −1.4 |
| Cucumber | 35 | 32 | 24 | −1.9 |

TABLE 3

The influence of seed priming treatments on tomato seedling emergence and growth.

| Treatment | Emergence % | T50 (days) | Dry wt. per plant (mg) |
| --- | --- | --- | --- |
| Nontreated | 87 b | 13.0 a | 4.25 c |

TABLE 3-continued

The influence of seed priming treatments on tomato seedling emergence and growth.

| Treatment | Emergence % | T50 (days) | Dry wt. per plant (mg) |
|---|---|---|---|
| Agro-Lig | 98 a | 9.1 c | 8.36 a |
| Soft coal | 95 ab | 9.6 c | 8.23 a |
| Sphagnum moss | 95 ab | 9.4 c | 8.02 a |
| −0.10 MPa PEG | 98 a | 10.5 b | 7.02 b |
| 1.0% KNO₃ and 1.5% K₃PO₄ | 95 ab | 9.1 c | 8.16 a |

LSD (5%)

Priming carrot seeds with inorganic salts resulted in lower percentage seedling emergence (Table 4). Faster seedling emergence (lower T50) was obtained from sowing SMP seeds with Agro-Lig. Sowing onion seeds after SMP with Agro-Lig decreased the T50 and increased the plant dry weight compared to all other treatments (Table 5).

Thermodormancy

The beneficial effects of SMP has already been shown by sowing crops into a cool soil environment. Short term priming treatments were also studied to alleviate thermodormancy in lettuce. Imbibing non-primed seeds at 35° C. resulted in 1% germination (Table 6). Conventional priming treatments and SMP with Agro-Lig were able to alleviate thermodormancy.

The attainment of a threshold seed water content is most important for seed priming (Table 2). The water potential of the medium is indirectly related to the seed moisture content (r=0.75). Bradford (1986, supra) primed lettuce seeds for 24 hours in −1.5 MPa PEG. The seed moisture content was ca 70% which is in close agreement with our data (Table 2). Similar data has been reported for carrot; seeds were incubated in −0.1 and −1.5 MPa PEG solution for 6 days which resulted in

TABLE 4

The influence of seed priming treatments of carrot seedling emergence and growth.

| Treatment | Emergence % | TSO (days) | Dry wt. per plant (mg) |
|---|---|---|---|
| Nontreated | 88 a | 10.8 a | 1.38 c |
| Agro-Lig | 89 a | 7.7 c | 2.17 a |
| 25% PEG | 87 a | 8.5 b | 1.89 b |
| 0.2 m KNO₃ + 0.1 m K₃PO₄ | 73 b | 8.1 b | 2.02 ab |

LSD (5%)

TABLE 5

The influence of seed priming treatments on onion seedling emergence and growth.

| Treatment | Emergence % | T50 (days) | Dry wt. per plant (mg) |
|---|---|---|---|
| Nontreated | 99 a | 11.0 a | 2.16 c |
| Agro-Lig | 98 ab | 6.0 c | 3.61 a |
| 34.2% PEG | 98 ab | 8.2 b | 2.93 b |

TABLE 5-continued

The influence of seed priming treatments on onion seedling emergence and growth.

| Treatment | Emergence % | T50 (days) | Dry wt. per plant (mg) |
|---|---|---|---|
| 0.2 m KNO₃ + 0.1 m K₃PO₄ | 95 b | 7.8 b | 2.87 b |

LSD (5%)

TABLE 6

The influence of seed priming treatments on lettuce permination at 35 C.

| Treatment | Treatment duration hours | Percent germination |
|---|---|---|
| Nontreated | — | 1 b |
| Agro-Lig | 24 | 75 a |
| −1.5 MPa PEG | 24 | 71 a |
| 1.0% K₃PO₄ | 20 | 71 a |

LSD (5%)

seed moisture contents of 76 and 68% respectively (Hegarty, 1977, *New Phytol.* 78: 349–359).

Results from the water potential components of Agro-Lig are very interesting. One would immediately expect that the major component responsible for water potential was psi-m which is attributed to the fact that Agro-Lig is similar to an organic soil. However, psi-m could account for less than 1.5% of the total. The major portion of water potential is psi-s which is atrributed to the Agro-Lig composition. Analysis of the Agro-Lig has revealed the presence of $10.2 \times 10^3$, $1.84 \times 10^3$ and $1.187 \times 10^3$ ug of calcium, magnesium and sodium, respectively per g of material.

Solute leakage from all seed kinds were found to contribute to the psi-s. In a separate study, tomato seeds were leached for 6 hours and then dried back to the original moisture content. SMP of these previously soaked seeds resulted in radical emergence. Thus, the osmotic effect of solute leakage from seeds during SMP does contribute to the water potential of the medium.

Determination of the optimal ratio of seed-solid matrix-water was performed on a empirical basis. It must be understood in this system that, unlike priming with solutions, there is not a large portion of solid matrix to seed. Thus as seeds imbibe and leak solutes the water potential of the medium changes. A simple screening procedure is used to obtain the optimal ratio of matrix, water and additives for a particular seedlot. There are several factors that influence this ratio. Seed characteristics include: threshold seed moisture content, affinity for water and the solute leakage. Agro-Lig characteristics include: innate chemical composition which influence the psi-s, the water holding capacity and water retention characteristics.

Seedling emergence and germination tests were conducted to evaluate the promotive effects of the pre-sowing treatments. Conventional priming treatments with PEG in inorganic salts were selected from the literature. Treatment comparisons with liquid priming treatments could better test the effectiveness of SMP. SMP with Agro-Lig was statistically equal to or better than conventional priming treatments for improving seedling emergence, decreasing T50 and increasing plant dry weight (Table 3, 4 and 5). Thermodormancy was shown to be alleviated with either SMP or liquid priming treatments (Table 6).

It is not fully understood why SMP is superior to conventional liquid priming treatments, however it is believed to be due to: (1) better aeration; (2) less phytotoxicity; and (3) the availability of growth promoting substances in the Agro-Lig. Humic acid is a naturally occurring plant growth regulator extracted from Agro-Lig (American Colloid Co.). Humic acid has been shown to stimulate seed germination and seedling growth in carrot (Ricotta and Sanders, *J. Am. Soc. Hort. Sci.* in press). Seedling root and shoot growth has been promoted with humic acid in wheat (*Triticum aestivum*) (Malic and Azam, 1985, *Environ. and Exp. Bot.* 25:245–252).

Similarly, it is not fully understood why synergistic results are achieved from the use of added microbes and chemicals during priming but such results are shown by tests, the results of which are provided in Tables 7 and 8. The data in Table 7 demonstrate synergism with regard to solid matrix priming and the utility of the technique in eliciting beneficial stand establishment effects when used with beneficial microorganisms in addition to the effect of either treatment alone. Other tests show that the systemic when added to the solid matrix priming system as well.

The data in Table 8 demonstrate that beneficial microorganisms act synergistically with solid matrix priming in conferring stand establishment benefits. Seedling carried further show superior resistance to damping off when treated with 1-102 in the solid matrix priming system. The differential of 30 to 40% increase in emergence due to treatment during priming has been found to be consistent. Similar data with beneficial pseudomonas, corynebacteria, enterobacter and bacillus species over a range of crops have been obtained.

The inoculation of seeds during matrix priming may be used as an inoculation system to introduce beneficial microbes into soil by inoculating seeds with beneficial microbes and permitting them to grow. In this specification, the words "beneficial microorganisms" or "beneficial microbes" means microorganisms inoculated by seeds and which are any of those many microbes that: (1) have been identified in association with plant roots, soils and seeds and/or as endophytes and determined to result in growth substance mediated plant growth promotion, improved plant nutrition and pest control through biocontrol and/or improved plant health to have potential utility in agriculture; (2) have been identified or can be further selected or engineered from those already identified to degrade specific chemical agents in soils to have potential utility in environment bioremediation if effectively delivered to the target site; and (3) are believed to be useful in supporting and protecting somatic embryos (synthetic seeds) as a substitute for zygotic seeds to deliver genetic characteristics of species which cannot be handled as zygotic seeds or to propagate elite germplasm and hybrids that are not now possible. The use of somatic embryos is described in Cantliffe DJ, Liu JR (1987), "Development of artificial seed of Sweet potato for clonal propagation through somatic embryogenesis in: Methane from biomass: A systems approach", Smith W H, Frank J R (eds) Elsevier, N.Y., pp 183–195.

Beneficial microbes in association with plants are ubiquitous in natural soil environments and serve useful functions in removing contaminants from the ecosystems. Such beneficial microbes are described in John Davison, "Plant Beneficial Bacteria", Bio/Technology, pages 282–284 and Chet, et al., "Mechanisms of biocontrol of soil-borne plant pathogens by Rhizobacterial", D. L. Keister and P. B. Cregan (Eds.), The rhizosphere and plant growth, 229–236. However, with the exception of Rhizobium and Bradyrhizobium genera, none of the many beneficial rhizosphere, soil or seed based microbes that have been identified has been extensively commercialized. The problem is not whether useful microbes can be identified but the economic delivery of a reproducibly useful inoculum at the target site.

The potential utility of beneficial microbes in managed terrestrial ecosystems for agriculture and environment bioremediation is substantially dependent on delivering adequate numbers of targeted beneficial microbes to the ecosystem site/niche where activity is needed at an economical cost.

However, it has been discovered that seed inoculation and the subsequent growth of the target microbe in the root environment provides an economical mechanism for delivering adequate numbers of beneficial microbes to a terrestrial environment. The bulk of the inoculum increase takes place using photosynthesis as energy and the rhizoplane, rhizosphere or plant endosphere as the bioreactor site.

Numerous genera of plant growth promoting rhizobacteria (PGPR) have been reported to have growth promotion

TABLE 7

Effect of *Serratia proteamacutans* Strain 1-102, solid matrix priming and chemical seed treatment an Canola seedling emergence in Pythium infested soil

| | Days After Planting % Emergence | | | | | | |
|---|---|---|---|---|---|---|---|
| Treatment | 1 | 2 | 3 | 4 | 5 | 6 | 7 |
| Untreated | 0 | 0 | 0 | 4 | 17 | 18 | 20 |
| SMP | 0 | 0 | 0 | 3 | 10 | 13 | 15 |
| Vitavax | 0 | 0 | 0 | 10 | 42 | 58 | 64 |
| 1-102 | 0 | 0 | 0 | 8 | 38 | 52 | 60 |
| SMP + 1-102 AP | 0 | 0 | 0 | 21 | 50 | 62 | 67 |
| SMP + 1-102 DP | 0 | 0 | 0 | 26 | 63 | 82 | 82 |

TABLE 7-continued

Effect of *Serratia proteamacutans* Strain 1-102, solid matrix priming and chemical seed treatment an Canola seedling emergence in Pythium infested soil

| | Days After Planting % Emergence | | | | | | |
|---|---|---|---|---|---|---|---|
| Treatment | 1 | 2 | 3 | 4 | 5 | 6 | 7 |

SMP = solid matrix priming in calcined clay and pH 6.8 phosphate buffer.
SMP + 1-102 AP = strain 1-102 added to the seeds after SMP.
SMP + 1-102 DP = strain 1-102 added during priming which was for a 3 day period.

TABLE 8

Effect of *Serratia proteamaculans* Strain 1-102, solid matrix priming and biological seed treatment on Cucumber seedling emergence in Pythium infested soil

| | Days After Planting % Emergence | | | | | | |
|---|---|---|---|---|---|---|---|
| Treatment | 1 | 2 | 3 | 4 | 5 | 6 | 7 |
| Untreated | 0 | 0 | 0 | 0 | 0 | 0 | |
| SMP | 0 | 1 | 10 | 20 | 23 | 22 | |
| 1-102 | 0 | 0 | 1 | 2 | 8 | 8 | |
| SMP + 1-102 AP | 0 | 3 | 15 | 50 | 48 | 43 | |
| SMP + 1-102 DP | 2 | 8 | 58 | 79 | 80 | 80 | |

SMP = Solid matrix priming in calcined clay and pH 6.8 phospate buffer.
SMP + 1-102 AP = strain 1-102 added to the seeds after SMP
SMP + 1-102 DP = strain 1-102 added during priming and biocontrol activity (Schroth and Hancock, 1981). Their review was over a decade ago and many other reports have been made since that time. However, PGPR usually fail in the field because of poor bacteria distribution on roots and failure of their antagonistic activity toward detrimental rhizosphere microbes (Schippers, et. al., 1987). It is generally believed that a critical threshold population of a particular

TABLE 10

Effect of Allelix's *Serratia proteamaculans* strain 1-102 and solid matrix priming on percentage cucumber seedling emergence in Phythium-infested soil

| Treatment | Days after planting | | | | | |
|---|---|---|---|---|---|---|
| | 1 | 2 | 3 | 4 | 5 | 6 |
| Untreated | 0 | 0 | 0 | 0 | 0 | 0 |
| SMP | 0 | 1 | 10 | 20 | 23 | 22 |
| 1-102 | 0 | 0 | 1 | 2 | 8 | 8 |
| SMP + 1-102 AP | 0 | 3 | 15 | 50 | 48 | 43 |
| SMP + 1-102 DP | 2 | 8 | 58 | 79 | 80 | 80 |

SMP = solid matrix priming in SMP media no. 2 and pH 6.8 phosphate buffer.
SMP + 1-102 AP = strain 1-102 added to the seeds after SMP.
SMP + 1-102 DP = strain 1-102 added during priming.

PGPR must be established to be effective and the method of application is critical (Weller, 1988). The solid matrix seed priming (SMP) process and a solid matrix seed priming based microbial inoculation process (SMPI) which has been effective in establishing large PGPR numbers on seeds and has resulted in effective seedling establishment in disease stress situations as shown in Table 10 (Table 1, Eastin, 1987, Solid matrix priming of seeds with microorganisms and selected chemical treatment, U.S. patent application Ser. No. 07/440,470; Eastin and Harman, 1987, Biological control and solid matrix priming, U.S. patent application Ser. No. 034,813). The data in table 10 are representative of results with *Pseudomonas flourescens, Pseudomonas putida, Enterobacter cloacae* and *Trichoderma* strains that have been tested. It can be understood from this table that there is a large differential achieved if bacteria are applied during priming as contrasted to after priming. It is believed the superior emergence response from SMPI under disease pressure as shown in Table 10 is a function of bacterial colonization of the seeds as contrasted to the lesser response with equivalent numbers of the same bacteria applied topically.

The SMPI system is based on the concept that microbes function in nature as colonies and the SMPI process provides microorganisms the opportunity to grow and colonize on hydrated seed surfaces. Priming seeds and the process of growing microbes on seeds during priming synchronizes radicle emergence and seedling development better with microbial activity from colonies established on the seed. The large log increase in bacteria numbers in/on the seeds appears to mean that low inoculum levels can result in large seed bacteria population if the proper inoculation system is used. This has large economic implications as inoculum can be increased by growing on the seed per se.

To inoculate soil with a beneficial microbe of any of the types described above, seeds are primed by mixing with the seeds a particulate solid matrix material and a seed priming amount of water, for a time and at a temperature sufficient to cause the seeds to imbibe sufficient water to enhance resultant plant vigor but insufficient to cause seed sprouting wherein said mixture has a water potential between about −0.5 to about −2.0 megapascals at equilibrium with said seeds and said particulate solid matrix material is nonpathogenic to the seeds and to the beneficial microbes. The primed seeds are planted under conditions not within one of said threshold germination moisture range and threshold germination moisture range for the unprimed seeds of the same species but within said range for the primed seed, wherein the beneficial microorganism is grown on the seed and matrix during priming matrix material and is planted with the seed and the seeds and soil are innoculated with a beneficial microorganism. The priming process is selected to be suitable for the beneficial microorganism. Thus, after colonizing the seed and matrix, the beneficial microorganism is present in colony numbers on the seed and carried to the soil.

In some cases, harmful agents can be destroyed or rendered ineffective during priming by antibiosis. For example, *Psuedomonas gladioli* which is a fungistatic bacteria has been inoculated onto sweet corn seeds by introduction in moisture during solid matrix priming and killed during dry back and storage. It acted as a powerful fungicide against Pennicilium and Fusarium species, thus SMPI can serve as an effective seed treatment process as well as a vehicle for effective seed and soil beneficial microbe inoculation.

While a preferred embodiment of the invention has been described with some particularity, many modifications and variations in the preferred embodiment may be made without deviating from the invention. Accordingly, within the scope of the appended claims, the invention may be practiced other than as specifically described.

What is claimed is:

1. A method of inducing into seeds systemic acquired resistance to pathogens during seed conditioning which comprises the steps of:

admixing with continuous aeration of seeds, a particulate solid matrix material and a seed priming amount of water, for a time and at a temperature sufficient to cause the seeds to imbibe sufficient water to enhance resultant plant vigor but insufficient to cause seed sprouting; and adding the pathogen.

2. Seeds primed by the process of claim 1.

3. A seed priming composition adapted to prime seeds which comprises a particulate solid matrix material and a seed priming amount of water proportioned to permit continuous aeration of seeds, said mixture having a water potential sufficient to cause a desired predetermined seed, when contacted with said composition and a pathogen, to imbibe sufficient water to enhance resultant plant vigor but insufficient to cause seed sprouting to obtain systemic acquired resistance to the pathogen.

4. A planting method comprising the steps of:

priming seeds by mixing with the seeds a particulate solid matrix material and a seed priming amount of water with sufficient aeration, for a time and at a temperature sufficient to cause the seeds to imbibe sufficient water to enhance resultant plant vigor but insufficient to cause seed sprouting including a pathogen for a sufficient time to induce systemic resistance to the pathogen;

drying the matrix;

planting the primed seeds under conditions not within one of a threshold germination temperature range and a threshold germination moisture range for the unprimed seeds of the same species but within at least one of a threshold germination temperature range and a threshold germination moisture range for the primed seed.

5. A method according to claim 4 in which the matrix material is removed before planting the seed.

6. A method according to claim 4 in which the matrix material is planted with the seed.

7. A method according to claim 4 in which the matrix material is colored with a distinctive color.

* * * * *